(12) United States Patent
Wolfgram et al.

(10) Patent No.: US 10,160,062 B2
(45) Date of Patent: Dec. 25, 2018

(54) LUMINESCENT BRAZE PREFORMS

(71) Applicant: Lucas-Milhaupt, Inc., Cudahy, WI (US)

(72) Inventors: Lawrence A. Wolfgram, Waukesha, WI (US); Alan Belohlav, Oostburg, WI (US)

(73) Assignee: Lucas-Milhaupt, Inc., Cudahy, WI (US)

( * ) Notice: Subject to any disclaimer, the term of this patent is extended or adjusted under 35 U.S.C. 154(b) by 0 days.

(21) Appl. No.: 14/981,008

(22) Filed: Dec. 28, 2015

(65) Prior Publication Data

US 2016/0158895 A1 Jun. 9, 2016

Related U.S. Application Data

(62) Division of application No. 14/344,533, filed as application No. PCT/US2012/056906 on Sep. 24, 2012, now abandoned.

(Continued)

(51) Int. Cl.
  *B23K 31/02* (2006.01)
  *B23K 35/00* (2006.01)
  (Continued)

(52) U.S. Cl.
  CPC .......... *B23K 35/00* (2013.01); *B23K 1/0006* (2013.01); *B23K 1/008* (2013.01); *B23K 1/20* (2013.01);
  (Continued)

(58) Field of Classification Search
  CPC ...... B23K 35/00; B23K 31/02; B23K 1/0006; B23K 1/008; B23K 35/0222;
  (Continued)

(56) References Cited

U.S. PATENT DOCUMENTS 3,406,285 A * 10/1968 Scorgie .................. C09K 11/06
  148/23
3,557,015 A * 1/1971 Alburger .................. C09D 5/22
  106/31.15

(Continued)

FOREIGN PATENT DOCUMENTS

CN   202885032 U *  4/2013
EP    2574420 A1 *  4/2013 ........... B23K 1/0012

(Continued)

OTHER PUBLICATIONS

Machine translation of JP 7-334643A (no date available).*
RD 275070A, Mar. 1987.*

*Primary Examiner* — Kiley S Stoner
(74) *Attorney, Agent, or Firm* — Boyle Fredrickson, S.C.

(57) ABSTRACT

A braze preform is provided that includes a filler metal and a luminescent material that covers at least a portion of the filler metal and that can luminesce when exposed to a black light. The luminescent material may include a luminescent ink and a solvent that are mixed together before being applied to filler metal. Presence of the braze preform may be determined using automated equipment by detecting luminescence of the braze preform with a sensor. A decision may be made on whether to advance a parts assembly for brazing based on the determination of presence or absence of the braze preform on such parts assembly.

14 Claims, 3 Drawing Sheets

Related U.S. Application Data

(60) Provisional application No. 61/538,448, filed on Sep. 23, 2011.

(51) Int. Cl.
| | | |
|---|---|---|
| *B23K 35/02* | (2006.01) | |
| *B23K 35/30* | (2006.01) | |
| *B23K 1/008* | (2006.01) | |
| *B23K 1/20* | (2006.01) | |
| *B23K 31/12* | (2006.01) | |
| *B23K 35/365* | (2006.01) | |
| *B23K 1/00* | (2006.01) | |
| *G01N 21/63* | (2006.01) | |
| *B23K 101/00* | (2006.01) | |

(52) U.S. Cl.
CPC .............. *B23K 31/02* (2013.01); *B23K 31/12* (2013.01); *B23K 35/02* (2013.01); *B23K 35/0222* (2013.01); *B23K 35/302* (2013.01); *B23K 35/365* (2013.01); *G01N 21/63* (2013.01); *B23K 2101/00* (2018.08); *G01N 2201/061* (2013.01); *Y10T 428/12493* (2015.01); *Y10T 428/218* (2015.01); *Y10T 428/31678* (2015.04)

(58) Field of Classification Search
CPC ........ B23K 35/365; B23K 31/12; B23K 1/20; B23K 35/30; B23K 35/02; B23K 2201/00; G01N 21/63; G01N 2201/061; Y10T 428/12493; Y10T 428/218; Y10T 428/31678
USPC .................. 228/102–105, 218–220, 8–12, 42
See application file for complete search history.

(56) References Cited

U.S. PATENT DOCUMENTS

| | | | | | |
|---|---|---|---|---|---|
| 3,656,951 | A | * | 4/1972 | Anderson | G03F 7/038 430/271.1 |
| 4,183,767 | A | * | 1/1980 | Kessler | C09D 5/00 106/236 |
| 4,260,675 | A | * | 4/1981 | Sullivan | B23K 35/224 355/132 |
| 4,410,562 | A | * | 10/1983 | Nemoto | B41M 3/008 427/259 |
| 4,670,298 | A | * | 6/1987 | Lucas | B23K 35/22 148/23 |
| 5,179,933 | A | * | 1/1993 | McCrillis | F23N 5/022 110/212 |
| 5,820,697 | A | * | 10/1998 | Hamilton | B23K 3/08 148/23 |
| 6,311,538 | B1 | * | 11/2001 | Martin | G01N 21/91 250/252.1 |
| 6,536,649 | B1 | * | 3/2003 | Master | H01L 21/67253 134/1.1 |
| 6,743,281 | B1 | * | 6/2004 | Miller | B01D 46/0086 116/DIG. 25 |
| 8,070,482 | B2 | * | 12/2011 | Fuentes | F23N 3/002 236/14 |
| 9,261,437 | B2 | * | 2/2016 | Kashima | G01N 1/22 |
| 2002/0146657 | A1 | * | 10/2002 | Anderson | B23K 1/008 432/11 |
| 2003/0131841 | A1 | * | 7/2003 | Anschutz | F24C 15/008 126/213 |
| 2010/0163098 | A1 | * | 7/2010 | Clemens | B23K 35/02 136/246 |
| 2012/0175404 | A1 | * | 7/2012 | Lai | H01L 24/80 228/102 |
| 2012/0180776 | A1 | * | 7/2012 | Newsom | F24C 15/022 126/197 |
| 2013/0248583 | A1 | * | 9/2013 | Kim | B23K 3/08 228/105 |
| 2014/0238106 | A1 | * | 8/2014 | Kashima | G01N 1/2202 73/23.2 |
| 2015/0233796 | A1 | * | 8/2015 | Kashima | H01J 49/0422 250/288 |

FOREIGN PATENT DOCUMENTS

| | | | | | |
|---|---|---|---|---|---|
| JP | 02297048 | A | * | 12/1990 | |
| JP | 07334643 | A | * | 12/1995 | |
| JP | 2003065958 | A | * | 3/2003 | |
| JP | 2011035218 | A | * | 2/2011 | |
| JP | 2011169753 | A | * | 9/2011 | ........... G01N 21/643 |
| JP | 2011237204 | A | * | 11/2011 | |
| JP | 2013040825 | A | * | 2/2013 | |
| JP | 5684674 | B2 | * | 3/2015 | |

\* cited by examiner

LUMINESCENT BRAZE PREFORMS

CROSS-REFERENCE(S) TO RELATED APPLICATION(S)

This application is a divisional application of U.S. Ser. No. 14/344,533, filed on Mar. 12, 2014, which is a national stage application of PCT/US2012/056906 filed on Sep. 24, 2012, which claims priority to U.S. provisional application No. 61/538,448 filed on Sep. 23, 2011. The entire contents of all are hereby expressly incorporated by reference into the present application.

FIELD OF THE INVENTION

The invention relates generally to brazing products and, in particular, to braze preforms.

BACKGROUND OF THE INVENTION

Braze preforms, which are brazing materials that are formed into shapes by a manufacturer, are known. Automating assembly procedures are known and widely implemented. Furthermore, brazing is known to produce a brazed joint that is obtained by joining metals and alloys at temperatures higher than 800 degrees Fahrenheit but less than the melting temperatures of the joined parts.

SUMMARY OF THE INVENTION

The present inventors have recognized that automating brazing procedures can be difficult because, although automating assembly of braze preforms onto components being brazed is known, it is difficult to confirm whether such assembly has actually taken place prior to brazing. The present inventors have recognized that during automated brazing procedures, components are heated during a brazing process, unfortunately, without braze preforms actively being assembled to the components. However, the absence of braze preforms may not be discovered until the components fail a post-brazing test or during use in the field. The present inventors have further recognized that even during automated brazing procedures, such confirmation is typically done by an operator visually inspecting the components to see whether the braze preforms are physically there. Nevertheless, further eliminating this human operator visual inspection may be desirable. The present inventors have also recognized that while sensors may be able to detect known braze preforms by optical or mass sensing, these would have to be highly sophisticated and correspondingly expensive to initially purchase and maintain.

The present inventors have further recognized that inks which may make braze preforms relatively more visually conspicuous are generally incompatible with brazing procedures and may contaminate the flux or the pool of filler metal during a brazing procedure and/or otherwise compromise the integrity of the brazed joint. Therefore, the present invention contemplates a braze preform and corresponding brazing systems and/or methods that address these and other inventor-identified problems and drawbacks of the prior art.

Thus, in accordance with an aspect of the invention, a braze preform is provided that includes a filler metal and a luminescent material that can luminesce when exposed to a special light; the luminescent material covering at least a portion of the filler metal. The luminescent material may include a luminescent ink and a solvent that are mixed together before being applied to the filler metal, so as to provide a diluted luminescent covering for the braze preform. The luminescent ink may be a neon blue ink, but may be any optical brightener. The optical brightener is the active material that causes the luminescence under a black UV light. The optical brightener may also be made up of a powder including various volatile solvents as well as a hardener to adhere the optical brightener to the surface of the preform in order to prevent the luminescent material from falling off during material handling. The hardeners may also include acrylics . . . . The solvent may be a non-flammable, optionally other, solvent that may be highly volatile and/or fast drying such as MEK solvent, which is flammable. The luminescent ink and solvent may both be liquids that are mixed together before their application upon the braze preform. Preferably, a hardener is used in the mixture, although a hardener in the solution may not always be necessary.

The luminescent ink may be about 30% of the weight of the luminescent material before being applied to the filler metal and the solvent is about 70% of the weight of the luminescent material before being applied to the filler metal. The luminescent ink may be about 10-50% of the weight of the luminescent material before being applied to the filler metal. The solvent may be about 50-90% of the weight of the luminescent material before being applied to the filler metal. This may provide a highly diluted luminescent material as a coating that overlies the braze preform or at least its filler metal, directly or indirectly, based on the particular configuration of the braze preform. The resultant coating of luminescent material may be substantially thin, for example, in an embodiment in which substantially the entire solvent portion of the luminescent material evaporates after the luminescent material is applied to the preform or at least its filler metal. The substantially thin coating of the luminescent material may provide a relatively small amount of the luminescent ink and correspondingly a relatively small amount of non-filler metal material which may reduce the likelihood of braze joint contamination. The luminescent material, when applied to a brazing preform, may be less than 0.15% total weight of the braze preform after the luminescent material is fully cured.

Controlling the total weight of the luminescent material to equal to or less than 0.15% prevents contamination from occurring when the preform is brazed. For example, when the brazing preform is heated, the filler metal and the flux are melted to form a braze pool. The flux works to remove oxides from the parent metals and allow the braze pool to properly bond to the parent metals. Typically, adding any additional material to the braze pool will cause contamination to form. Contamination may include inclusions, voids, porosity, slag, spatter, or any other phenomena that weakens the strength of a braze joint. The luminescent material is unique in the fact that its presence will not introduce contamination to the braze pool.

To verify that the brazed part is free of defects, including contamination, many different inspection methods may be employed. These inspection methods may include test strength testing, temperature testing, and helium mass spectrometer leak detection. Helium mass spectrometer leak detection systems work as follows: helium is introduced to a test part that is connected to a leak detector. The helium travels through brazed part and if there is contamination that produces a leak, the helium enters into the leak detector. The helium's partial pressure is sensed and results are displayed on the leak detector as a flow rate. The higher the flow rate, the larger the detected leak will be.

Other forms of testing the brazed part include burst testing. When burst testing, the brazed part is subjected to an internal pressure. This pressure may be for example within a copper pipe that is brazed to a brass valve body. A pressure is introduced to the copper pipe and brass valve body and the brazed part should withstand a pressure of 2,500 psi minimum. Typical testing has; however, produced brazed parts that withstand 3,000-4,000 psi without bursting. While a strong, brazed part may withstand the minimum 2,500 psi burst pressure test, leak testing a brazed part to 400 psi minimum may also be employed to verify there are no leaks.

Common parent metals used, also called base metals, in the brazing application include brass and copper. Brazed joints may produce a copper to copper joint, a brass to brass joint, or a brass to copper joint. Brass parts may include 360 brass alloy and copper parts may include CDA 122 copper pipe. 360 brass is commonly known to have a 58,000 psi tensile strength while CDA 122 copper, when annealed through the brazing process, is known to have a 32,000 psi tensile strength. A proper brazed part will be at least 90% as strong as the base metal part, but preferably just as strong. This means that when brazing 360 brass to CDA 122 copper pipe, the brazed joint should preferably withstand a 32,000 psi tensile strength test. The addition of the luminescent material disclosed herein will not introduce any imperfection, impurity, or contamination to the brazed part. A typical imperfection, contamination, or impurity that occurs when items are introduced to the braze pool will traditionally cause any one of the above mentioned tests to fail.

Additionally, brazed parts are commonly used in the heating, ventilation, and air conditioning field. Certain parts in this field, such as thermostatic valves, may include various brazed parts. Refrigerants may also be flowed through these parts that include R-22 refrigerant or R-410 refrigerant. These refrigerants are known to operate at temperatures including a minimum of 80 degrees Fahrenheit, on the low pressure side, and a minimum of 125 degrees Fahrenheit on the high pressure side. The brazed parts must therefore be able to withstand such operating conditions.

In accordance with another aspect of the invention, a system is provided that may be used to detect presence or absence of a braze preform by detecting the luminescent material that at least partially covers, directly or indirectly, the filler metal. The system may include a light source emitting light that can cause the luminescent material of the braze preform to luminesce and a sensor that can detect luminescence. The light source may be a black light. The sensor is positioned so as to detect the luminescence of the braze preform, for example, facing the component(s) upon which the braze preform is assembled. The sensor may be a UV sensor or other suitable sensor that can detect luminescence of the luminescent material.

In accordance with another aspect of the invention, a method of determining whether to perform a brazing procedure is provided. The method includes treating a braze preform with a luminescent material and assembling the braze preform to a component to be subjected to a brazing procedure. A light is directed toward the component to be subjected to a brazing procedure and the luminescent material at the parts assembly is detected. Presence or absence of the brazing preform on the component is determined based on the detection or non-detection of the luminescent material. A determination is made on whether to perform a brazing procedure based on the detection or non-detection of the luminescent material and thus the presence or absence of the braze preform. Presence or absence of the braze preform may be detected after the braze preform is supposed to be assembled to a single component that will be brazed or after the braze preform is supposed to be assembled to a parts assembly having multiple components assembled to each other and that will be brazed to each other. Detecting of the presence or absence of the braze preform may be performed in a lit environment and thus under the overhead or other lighting of a facility in which the assembly and brazing takes place. Detecting of the presence or absence of the braze preform may be performed in a darkened environment in which relatively less of the overhead or other lighting of the facility illuminates the component(s) that will be brazed. The darkened environment may be achieved by blocking at least some of the overhead or other lighting of the facility with a shield. Multiple shields may be interconnected to define an enclosure that blocks at least some of the overhead or other lighting of the facility so as to create a darkroom-type environment in which the detection of the presence or absence of the braze preform may be performed. This may allow relatively less sophisticated sensors to be used for detecting the presence or absence of the luminescent material and thus also the presence or absence of the braze preform. When presence of the braze preform is detected, the component(s) to be brazed may be allowed to advance for further assembly or other processing, and/or brazing which may occur in a brazing furnace.

Numerous other aspects, features, and advantages of the present invention will be made apparent from the following detailed description taken together with the drawing figures.

BRIEF DESCRIPTION OF THE DRAWINGS

The drawings illustrate the best mode currently contemplated of practicing the present invention.

In the drawings:

FIG. 1b is a continuation of the schematic representation of the system in accordance with the present invention described in FIG. 1a.

DETAILED DESCRIPTION OF THE INVENTION

Figure 1A:
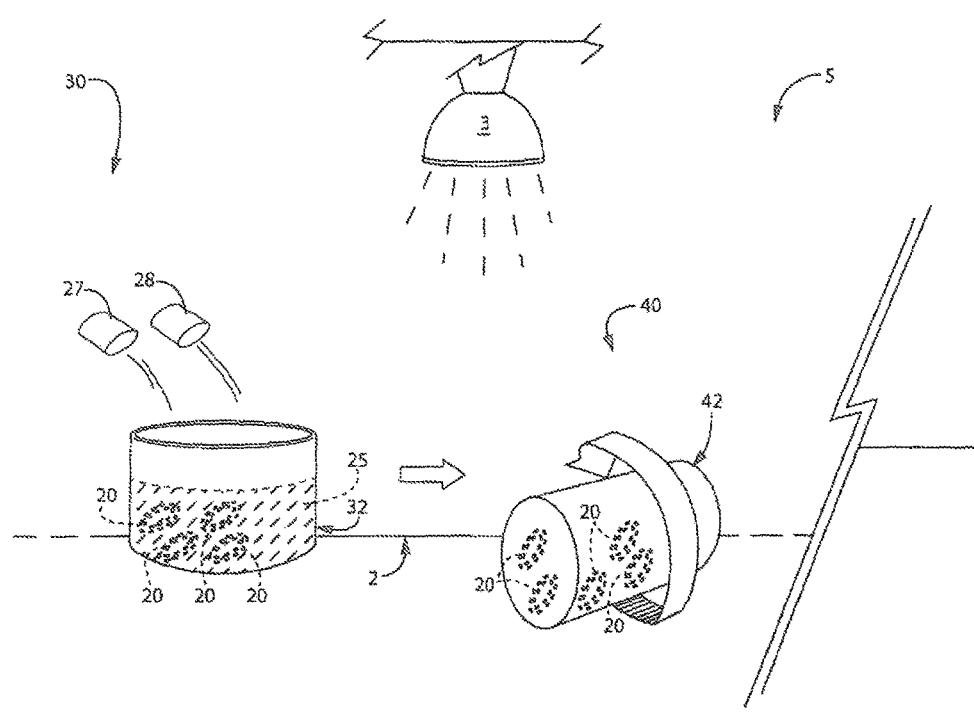
FIG. 1a is a schematic representation of a system in accordance with the present invention.
Figure 1B:
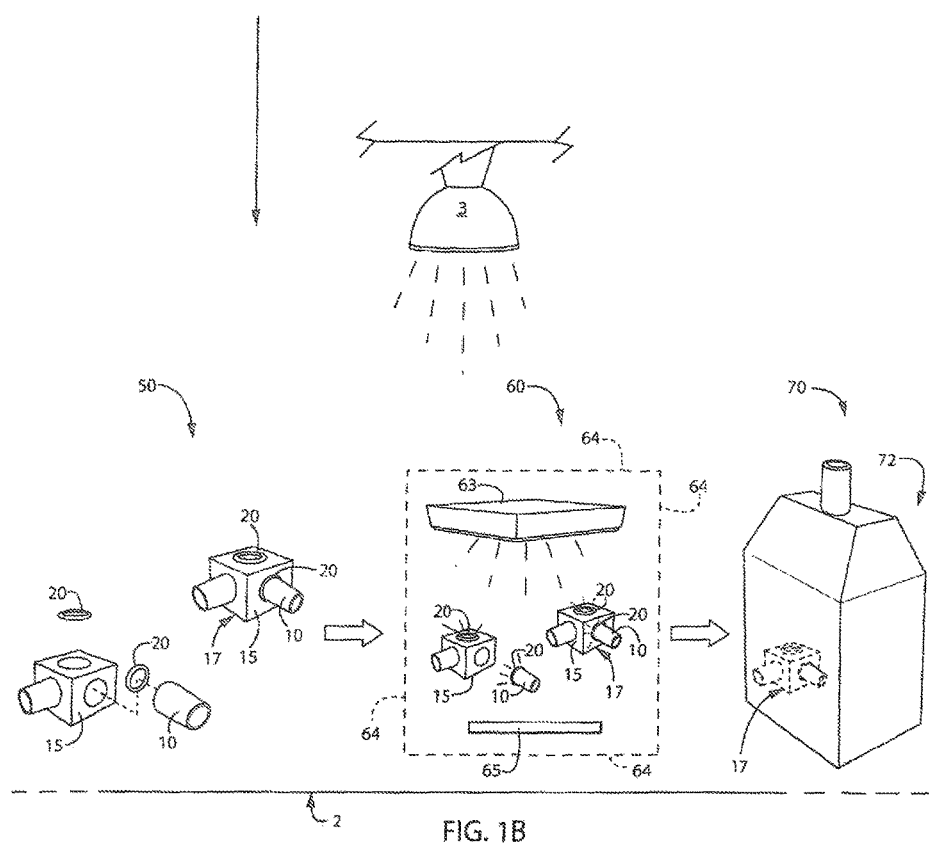

FIGS. 1a-1b illustrate a system 5 that is provided within a facility 2 and that can be used for brazing components 10, 15 to each other using a braze preform 20. In a representative application, the system 5 includes a preparation station 30 and a drying station 40 that are used for coating a luminescent material 25 over a filler metal 22 (FIG. 2) of the braze preform 20, explained in greater detail elsewhere herein. Assembly station 50, a detecting station 60, and a brazing station 70 are also provided in the facility 2. In a preferred embodiment, the preparation and drying stations 30, 40 are provided in a first facility 2 and the assembly, detecting, and brazing stations 50, 60, and 70 are provided in a separate facility (not shown). This may allow a manufacturer of the braze preforms 20 to treat and/or coat the braze preforms 20 with the luminescent material 25 and then provide such braze preforms 20 to a different manufacturer to use in brazing the components 10, 15 to each other using the rest of the system 5. The system 5 is configured so that presence or absence of a braze preform 20 on a component 10, 15 can be automatically determined by detecting the luminescence of the braze preform 20. This allows a yes or no decision;

that is, continuing to a brazing procedure or a reject decision can be automatically made, as described in greater detail elsewhere herein.

Figure 2:
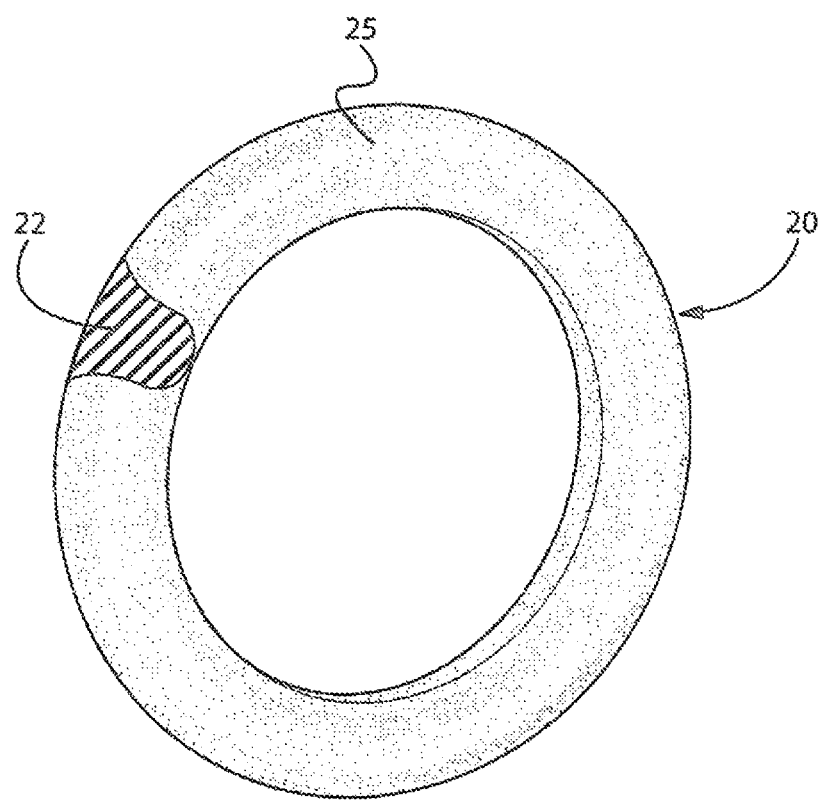
FIG. 2 is a partially cut-away isometric view of a braze preform in accordance with the present invention.

Referring now to FIG. 2, braze preform 20 includes a filler metal 22, such as aluminum, stainless steel, carbon steel, brass, copper, or any other metal or alloy, that is coated with the luminescent material 25 and which may define a brazing ring configuration or have other preformed configurations, depending on the particularly desired end-use. Suitable brazing rings or valves (such as for HVAC equipment), may be coated with the mixture, and/or other preformed brazing products which are suitable for use as filler metal 22 are available from Lucas-Milhaupt, Inc., having a place of business in Cudahy, Wis., U.S.A. under the trade names Sil-Fos® for brazing components 10, 15 that are made from copper-based materials, and Braze™ and Easy-Flo® for brazing components 10, 15 that are made from steels, stainless, and/or other ferrous materials. The filler metal 22 may be flux coated or cored, for example, as described in the commonly owned U.S. Reissue Pat. No. RE 42,329 entitled Flux Cored Preforms for Brazing, and pending U.S. application Ser. No. 12/324,410 entitled Brazing Material Containing A Flux which was filed Nov. 26, 2008 and pending U.S. application Ser. No. 12/602,053 entitled Brazing Material which was filed Jan. 5, 2011, all of which are incorporated by reference herein, in their entireties.

Referring again to FIGS. 1a-1b, the luminescent material 25 in this embodiment includes multiple liquid constituents, namely, a luminescent ink 27 and a solvent 28. The solvent may be bromide based and include the non chlorine based N-TRON solvent. Luminescent ink 27 and solvent 28 are mixed together in a container 32 at the preparation station 30. Luminescent ink 27 includes any color, for example, a neon blue color, ink and the solvent 28 of this embodiment is a non-flammable, optionally other, fast-drying solvent(s). One suitable brightener is sold by www.blacklightworld.com. It is contemplated that the luminescent ink 27 can be red or some other color. Preferably, the luminescent ink 27 is invisible to the naked eye after application. That is, luminescent ink 27 preferably cannot be seen under ambient light or conventional incandescent, fluorescent, and/or other conventional lighting. The luminescent ink 27 need not be an ink or even a liquid, per se, but can instead be a powder or other solid that can be transferred to and/or adhered to the braze preforms 20. This can be done by mixing such powder or solid form of the luminescent ink 27 into the solvent 28 to form a suspension for a liquid application. Optionally, the luminescent ink 27 may be applied to the braze preforms 20 in its powered or other solid form. The coating may be applied in any thickness, but preferably is thin as well as transparent under ambient light.

These are mixed in a ratio that highly dilutes the luminescent ink 27 by providing the luminescent ink 27 in a less than 50% by weight of the overall luminescent material 25. For example, a preferred embodiment has a ratio in which about 30% of the weight of the luminescent material 25 is the luminescent ink 27 and 70% of the weight of the luminescent material 25 is the solvent 28, while both the luminescent ink 27 and the solvent 28 are in liquid states in the container 32. In another embodiment, the luminescent ink 27 may be between about 10-50% of the weight of the luminescent material 25 and the solvent may be between about 50-90% of the weight of the luminescent material, before being applied to the braze preform(s) 20. Still referring to FIGS. 1a-1b, at preparation station 30, the luminescent material 25 is applied to a batch of multiple braze preforms 20 to allow each of the braze preforms 20 to luminesce. This is done by dipping, optionally soaking, the braze preforms 20 in the luminescent material within the container 32. The braze preforms 20 are then removed from the container 32 and placed in a tumbler 42 and/or other suitable drying device at drying station 40. The braze preforms 20 are agitated and tumbled in the tumbler 42 which mechanically removes some of the excess luminescent material 25, with the rest of the excess luminescent material 25 being removed by, e.g., evaporation and/or volatile release of the solvent 28 constituent. This leaves a thin coating of the luminescent material on each of the braze preforms 20 which, in most embodiments, has a higher concentration of luminescent ink 27 within the luminescent material 25 on the braze preforms 20. In other words, there is a greater ratio of luminescent ink 27 versus solvent 28 as compared to the luminescent material in its fully liquid state in the container 32.

In another embodiment, the luminescent material 25 is applied to the braze preforms 20 by a spray application instead of by dipping, dunking, or soaking. In yet another embodiment, the application and drying are performed at the same time and/or by way of a single piece of application equipment. In such embodiment, the luminescent material 25 may be sprayed and dried at a single station, for example, by way of a combined tumbling, spray applying, and drying machine. One suitable machine is available under the trade name Rotamat coating machine from the Walther Trowal company of Belgium. The mixture with luminescent material 25 may also be sprayed on (with or without flux) in ambient or in a reduced atmosphere. In another embodiment, the luminescent material 25 may be integrated with other steps in the manufacturing process for making the braze preforms 20 themselves. In other words, the application of the luminescent material 25 may not require a separate application step(s). Instead, the luminescent material 25 may be mixed with the flux and/or other coating materials so that the luminescent material 25 is applied simultaneously with the flux and/or other coat materials as a component thereof.

Regardless of the particular way in which the luminescent material 25 is applied to the braze preforms 20, the luminescent material 25 may cover substantially the entire outer surface of the braze preform, for example, covering about 90%, plus or minus 10%. Or, the luminescent material 25 may cover a relatively smaller percentage of the outer surface of the braze preform 20. The luminescent material 25 may be placed at a single discrete location or multiple discrete locations that are spaced from each other on the outer surface of the braze preform 20. For embodiments of braze preforms 20 that include grooves, channels, and/or other structural features, the luminescent material 25 may be applied onto or into such grooves, channels, or other structural features, optionally adjacent such features as long as at least a portion of the luminescent material 25 can be detected by a sensor 65 as described in greater detail elsewhere herein. The coating of luminescent material 25, whether it be an entire coating, a partial coating, and/or discrete markings upon the braze preforms 20, is sufficiently hard, permanent, and can withstand shipping and handling with minimal losses. Stated another way, the luminescent material 25 upon the braze preforms 20 is permanent and will not wash off. The surface layer thickness of the coating of the luminescent material 25 is, in some embodiments, approximately the same thickness, plus or minus 10%, as would be an ink layer from a permanent marker applied to the braze preforms 20. Regardless, after leaving the preparation and/or drying stations 30, 40, the braze preforms 20 are luminescent and may be utilized elsewhere in the system 5.

Still referring to FIGS. 1a-1b, as shown at the left-hand side of assembly station 50, the braze preforms 20 are assembled onto the components 10, 15. As shown at the right-hand side of assembly station 50, multiple braze preforms 20 that are installed on a parts assembly 17 that is defined by components 10 and 15 that are assembled to each other. The braze preforms 20 are assembled onto the components 10, 15 and/or parts assembly 17 in a known automated manner. After such assembly, the components 10, 15 and/or parts assembly 17 are moved from the assembly station 50 to the detecting station 60.

Still referring to FIGS. 1a-1b, at detecting station 60, presence or absence of the braze preform 20 upon the components 10, 15 and/or parts assembly 17 is determined. In a preferred embodiment, the luminescent material is invisible 25 to the naked eye and/or under normal lighting conditions. In such embodiments, detecting station 60 includes a light source 63 that emits a different wavelength of light than is emitted from a facility light source 3. In this embodiment, the facility light source 3 is a conventional overhead florescent or incandescent light source, as is typical for a manufacturing-type facility 2. The preferred light source 63 is a black light, optionally another light that can suitably cause the luminescent material 25 and thus the braze preforms 20 to luminesce. Light source 63 is positioned with respect to the braze preforms 20 within the detecting station 60 so that light emitting from the light source 63 is directed toward the braze preforms 20. Sensor 65 is positioned within the detecting station 60 so as to allow the sensor 65 to detect luminescence from the luminescent material 25 and thus the braze preforms 20. A suitable sensor 65 is a UV sensor which is available from the Keyence Corporation of America, in Elwood Park, N.J., U.S.A. A UV meter reading may indicate a level of "8" (below 4 stops) to show the coating is present. In one embodiment, the sensor 65 detects luminescence and thus the presence of the braze preform 20 on a single component 10, 15, as illustrated at the left-hand side of detecting station 60. In another embodiment, the sensor 65 detects luminescence and thus the presence of the braze preform 20 on the parts assembly 17 after the components 10, 15 have been assembled to each other, such as that shown at the right-hand side of detecting station 60.

Still referring to FIGS. 1a-1b, in this embodiment, the detecting station 60 preferably provides a darkened environment in which luminescence detection occurs. The darkened environment in this embodiment is defined blocking at least some of the light from the facility light source 3 with multiple interconnected shields 64. Optionally, a single shield 64 may be used to enhance the ability of the sensor 65 to detect the luminescence and thus the presence of the braze preform 20. In another embodiment, no shields 64 are provided and the detection of luminescence is instead performed in a lit environment that is illuminated by the facility light source 3.

Regardless, if the sensor 65 does not detect luminescence of the luminescent material 25, a determination is made that the braze preform 20 is absent. When such absence of the braze preform 20 is determined, the component 10, 15 or parts assembly 17 is rejected and is not sent to the brazing station 70. If the sensor 65 does detect luminescence of the luminescent material 25, a determination is made that the braze preform 20 is present. When such presence of the braze preform 20 is determined, the component 10, 15 or parts assembly 17 is accepted and is sent to the brazing station 70, for example, a go/no go test may be used to prevent parts from proceeding that do not have the coated braze preform. For embodiments in which presence or absence of the braze preform 20 is determined on a component 10 or 15 instead of the parts assembly 17, if the presence of the preform 20 is determined on the component 10 or 15, then the components 10, 15 are assembled to each other to create the parts assembly 17 which is then sent to the brazing station 70 where a brazing procedure is performed.

The brazing station 70 includes a brazing furnace 72. The parts assembly 17 is placed in the brazing furnace 72 and the brazing furnace 72 is heated to a temperature required to heat the parts assembly 17 and melt the filler metal 22 of the braze preform 20 so as to join the components 10, 15 to each other by brazing. The applied mixture also does not leave any carbon residue when the material is burned during the brazing process. In the preferred embodiments in which the luminescent material 25 is invisible without being illuminated by the light source 63, any residual luminescent material 25 on the parts assembly 17 after the brazing procedure remains invisible or is non-staining of the components 10, 15. In view of the above, substantially an entire manufacturing process which includes a brazing procedure can be automated with system 5. It is understood that system 5 further includes various machines, logic controllers and other controllers, which are not discussed here because they are so well known to those skilled in the art.

Various alternatives are contemplated as being within the scope of the following claims particularly pointing out and distinctly claiming the subject matter regarded as the invention.

What is claimed is:

1. A method of joining multiple components by brazing, the method comprising:
 applying a luminescent material to a brazing filler metal;
 providing a first alloy piece;
 providing a second alloy piece;
 assembling the first alloy piece and the second alloy piece and brazing filler metal;
 directing a light from a light source toward the braze filler metal, the first alloy piece, and the second alloy piece;
 inspecting the luminescent material with a sensor;
 determining presence or absence of the brazing filler metal on one of the first and second alloy piece based on detection of the luminescent material; and
 performing a brazing procedure, based on a detected presence of the luminescent material, in a furnace between 1200-2000 degrees Fahrenheit for a period of time including 15 minutes or less thus brazing the multiple components together.

2. The method of claim 1, wherein the luminescent material is detected after the first and second components are assembled to each other and before the first and second components are brazed to each other.

3. The method of claim 1, wherein the brazing step occurs in a brazing furnace.

4. The method of claim 1, wherein at least one of the assembling steps is performed in an assembly station of a facility having a first light source and the detecting step is performed in a detecting station of the facility having a second light source that is different from the first light source.

5. The method of claim 4, wherein the second light source is an ultraviolet light.

6. The method of claim 1, further comprising blocking at least some light being emitted from the first light source with a shield that reduces the amount of light from the first light source that can illuminate the brazing filler metal.

7. The method of claim 6, wherein multiple interconnected shields define an enclosure that blocks at least some light being emitted from the first light source.

8. The method of claim 2, wherein the brazing the first and second components to each other step further includes producing a brazed joint free of luminescent material.

9. The method of claim 8, further comprising verifying the brazed joint is free of contamination with a helium leak check.

10. A method of inspecting and brazing a workpiece comprising the following process:
provviding a first alloy piece;
providing a second alloy piece;
providing a braze preform in contact with the first and second alloy piece forming the workpiece;
pre-treating the braze preform by spraying a luminescent material coating on an exterior of the braze preform;
directing an ultraviolet light toward the workpiece;
inspecting the luminescent material with a sensor;
determining presence or absence of the brazing preform on one of the first and second alloy piece based on detection of the luminescent material; and
performing at least one of not brazing the workpiece based on a detected absence of the luminescent material and brazing the workpiece based on a detected presence of the luminescent material.

11. The method of claim 10, further comprising burning off all of the luminescent material during the brazing.

12. The method of claim 10, further comprising using an automated sensor to automatically detect presence of the braze preform based on a detected presence of the luminescent material.

13. The method of claim 10, wherein the braze preform includes a core of flux material and wherein the luminescent material is an exterior coating applied to the braze preform separate from the flux material.

14. The method of claim 10, further comprising providing a flux material in a core of the braze preform.

* * * * *